US00PP12720P2

(12) United States Plant Patent
Leonard

(10) Patent No.: US PP12,720 P2
(45) Date of Patent: Jun. 25, 2002

(54) COREOPSIS PLANT NAMED 'SWEET DREAMS'

(75) Inventor: Mark Alan Leonard, New Castle, CA (US)

(73) Assignee: Yoder Brothers, Inc.., Barberton, OH (US)

( * ) Notice: Subject to any disclaimer, the term of this patent is extended or adjusted under 35 U.S.C. 154(b) by 11 days.

(21) Appl. No.: 09/761,473

(22) Filed: Jan. 18, 2001

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Coreopsis plant named 'Sweet Dreams', characterized by its large daisy-type inflorescences that are about 3.8 cm in diameter; unique purple and white bi-colored ray florets; very freely flowering habit with numerous inflorescences per plant; upright and outwardly spreading growth habit; very freely branching habit; and dark green foliage.

1 Drawing Sheet

BACKGROUND OF THE INVENTION

The present invention relates to a new and distinct cultivar of Coreopsis plant, botanically known as *Coreopsis rosea* and hereinafter referred to by the name 'Sweet Dreams'.

The new Coreopsis was discovered by the Inventor in a controlled environment in Loomis, Calif. on Jul. 5, 1996, as a naturally-occurring mutation of *Coreopsis rosea* cultivar American Dreams, not patented. The new Coreopsis was observed as a single plant in a group of flowering plants of the parent cultivar. The selection of this plant was based on its unique ray floret coloration.

Asexual reproduction of the new Coreopsis by terminal cuttings taken in a controlled environment in Loomis, Calif., has shown that the unique features of this new Coreopsis are stable and reproduced true to type in successive generations.

SUMMARY OF THE INVENTION

The cultivar Sweet Dreams has not been observed under all possible environmental conditions. The phenotype may vary somewhat with variations in environment such as temperarture, daylength and light intensity, without, however, any variance in genotype.

The following traits have been repeatedly observed and are determined to be the unique characteristics of 'Sweet Dreams'. These characteristics in combination distinguish 'Sweet Dreams' as a new and distinct cultivar:

1. Large daisy-type inflorescences that are about 3.8 cm in diameter.
2. Unique purple and white bi-colored ray florets.
3. Very freely flowering with numerous inflorescences per plant.
4. Upright and outwardly spreading growth habit.
5. Very freely branching.
6. Dark green foliage.

Plants of the new Coreopsis differ from plants of the parent cultivar American Dreams primarily in ray floret color as plants of the cultivar American Dreams have solid pink-colored ray florets. In addition, plants of the new Coreopsis are taller and have larger inflorescences than plants of the cultivar American Dreams.

BRIEF DESCRIPTION OF THE PHOTOGRAPHS

The accompanying colored photographs illustrate the overall appearance of the new Coreopsis, showing the colors as true as it is reasonably possible to obtain in colored reproductions of this type. Colors in the photographs may differ slightly from the color values cited in the detailed botanical description which accurately describe the colors of the new Coreopsis.

The photograph at the top of the sheet comprises a side perspective view of a typical flowering plant of 'Sweet Dreams'.

The photograph at the bottom of the sheet comprises a close-up view of typical inflorescences and leaves of 'Sweet Dreams'.

DETAILED BOTANICAL DESCRIPTION

In the following description, color references are made to The Royal Horticultural Society Colour Chart except where general terms of ordinary dictionary significance are used. The following observations and measurements describe plants grown in Keller, Tex. during the summer and fall under full sun and cultural conditions which approximate commercial practice. Plants used for the photographs and descriptions were grown as single plants in one-gallon containers and were about 9 to 10 months old. Measurements and numerical values represent averages for six flowering plants.

Botanical classification: *Coreopsis rosea* cultivar Sweet Dreams.

Parentage: Naturally-occurring whole plant mutation of *Coreopsis rosea* cultivar American Dreams, not patented.

Propagation:

*Type.*—Terminal tip cuttings.

*Time to initiate roots.*—Summer: About 7 to 12 days at temperatures of 23 to 29° C. Winter: About 10 to 14 days at temperatures of 15 to 20° C.

*Time to produce a rooted cutting.*—Summer: About 35 to 45 days at temperatures of 23 to 29° C. Winter: About 45 to 50 days at temperatures of 15 to 20° C.

*Root description.*—Fine and well-branched.

Plant description:

*Appearance.*—Perennial; upright and outwardly spreading; mounding habit.

*Plant size.*—Height: About 35 cm. Diameter or spread: About 52 cm.

*Lateral branch description.*—Very freely branching, usually two laterals will develop at every node; pinching is not required, however plants tend to be sturdier and more upright if pinched. Aspect: Initially upright, then outwardly arching. Strength: Moderate; stems will start to arch with the weight of inflorescences. Length: About 7.8 cm. Diameter: About 1 mm. Internode length: About 2.5 cm. Texture: Smooth, glabrous. Color: Medium green, 146A.

*Foliage description.*—Arrangement: Opposite, compound; sessile. Length: About 4.7 cm. Width: About 3.1 cm. Shape: 2 to 3-pinnate; leaflets linear. Apex: Acute. Base: Attenuate. Texture: Smooth, glabrous. Color: Young and mature foliage upper surface: Dark green, close to 147A. Young and mature foliage lower surface: Medium green, close to 146A.

Flowering description:

*Appearance.*—Daisy-type inflorescence form with roughly obovate-shaped ray florets. Inflorescences borne on terminals, arising from leaf axils. Disc and ray florets arranged acropetally on a capitulum. Inflorescences persistent.

*Flowering response.*—Under natural conditions, plant flower in the late spring after sufficient cool temperatures and continue to flower through the fall.

*Inflorescence longevity.*—Individual inflorescences last about one to two weeks.

*Quantity of inflorescences.*—Very freely flowering with more than 150 flower buds and inflorescences per plant.

*Inflorescence size.*—Diameter: About 3.8 cm. Depth (height): About 9 mm. Diameter of disc: About 9 mm.

*Fragrance.*—Faint; sweet, grass-like.

*Flower buds.*—Height: About 4.5 mm. Diameter: About 4.5 mm. Shape: Roughly spherical. Color: Tight bud, brownigh green, close to 199A with green, 148A, undertones; just before opening, grayed orange, 163A, with subsequent development becoming darker to 167A and eventually to 172A.

*Ray florets.*—Shape: Roughly obovate. Length: About 2 cm. Width: About 8 mm. Apex: Mamillate or emarginate; fringed appearance. Base: Attenuate. Margin: Entire. Texture: Smooth, satiny, glabrous. Aspect: Initially upright; when mature, about 90° from vertical, perpendicular to peduncle. Number of ray florets per inflorescence: About 8 arranged in a single row. Color: When opening and fully opened, upper surface: Center and apex, white, 155D, overlain with longitudinal stripes and random spots of purple, 61A to 71A; base, purple, more purple than 59A to 71A. When opening and fully opened, lower surface: White, 155D, underlain towards base with purple, close to 77A, longitudinal stripes.

*Disc florets.*—Arrangement: Massed at the center of the inflorescence. Shape: Tubular, flared at apex. Length: About 5 mm. Width: Apex: About 1 mm. Base: Less than 1 mm. Number of disc florets per inflorescence: About 45. Color: Immature: Slightly more green than 163A. Mature: Apex: Slightly more golden yellow than 172A to close to 44A; iridescent. Mid-section: Close to 9A. Base: 155D.

*Peduncle.*—Strength: Strong, wiry. Aspect: Angled about 40° from vertical. Length: About 2.2 cm. Diameter: Less than 1 mm. Texture: Smooth, glabrous. Color: 146A.

*Involucral bracts.*—Quantity: About 8 arranged in two rows. Length: About 6.5 mm. Width: About 3 mm. Texture: Smooth, waxy. Color, both surfaces: Apex, close to 163A to 167A to 172A; base, close to 148A.

*Reproductive organs.*—Androecium: Present on disc florets only. Anther color: 15A. Amount of pollen: Scarce to moderate. Color: 15A. Gynoecium: Present on both ray and disc florets.

*Seed.*—Seed production has not been observed.

Disease resistance: Resistance to pathogens common to Coreopsis has not been observed on plants grown under commercial conditions.

Temperature tolerance: Plants of the new Coreopsis have demonstrated good tolerance to night temperatures as low as −20° C. and day temperatures as high as 42° C.

It is claimed:

1. A new and distinct cultivar of Coreopsis plant named 'Sweet Dreams', as illustrated and described.

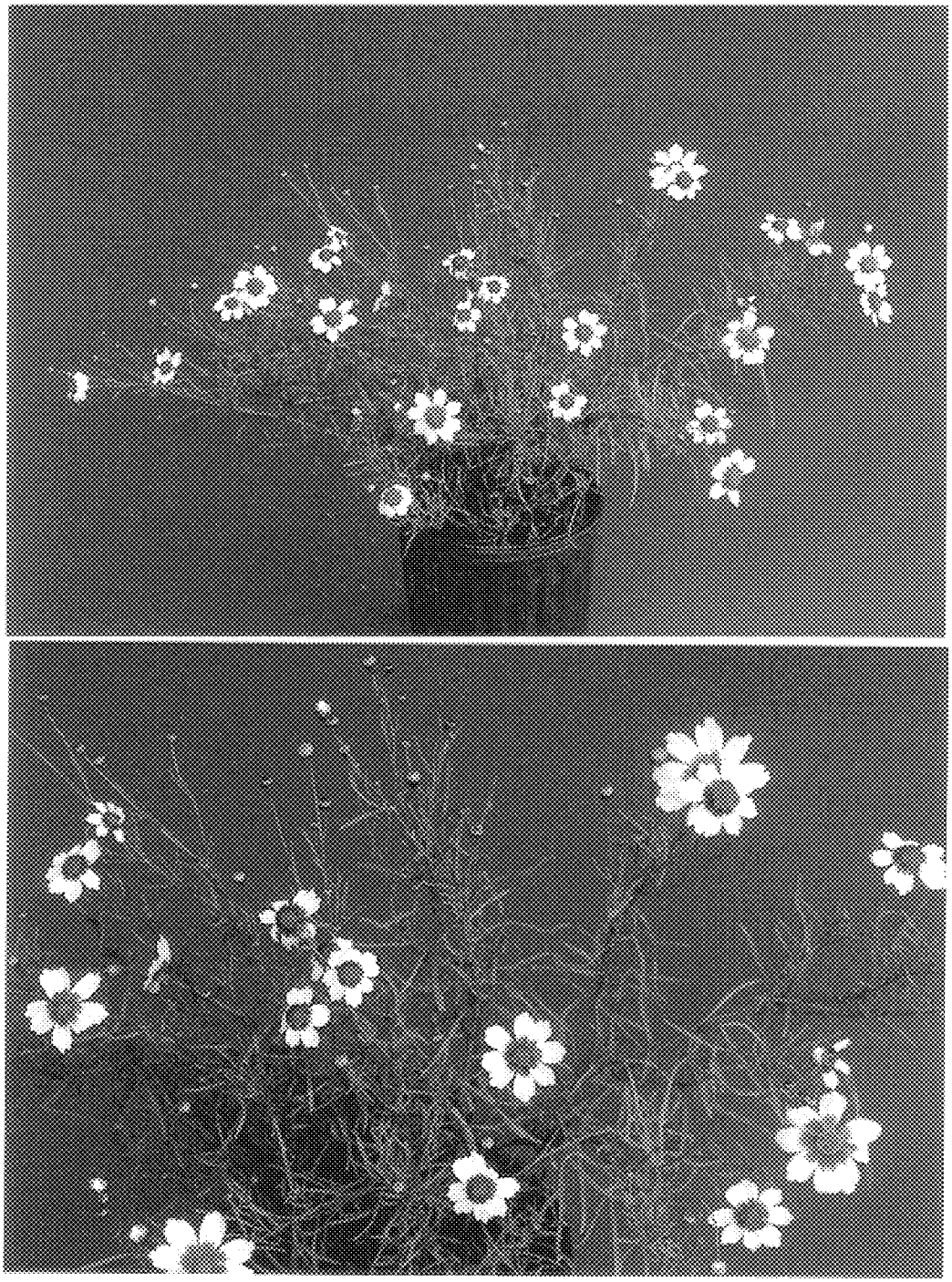

* * * * *